United States Patent [19]

Fletcher et al.

[11] 4,078,175

[45] Mar. 7, 1978

[54] APPARATUS FOR USE IN EXAMINING THE LATTICE OF A SEMICONDUCTOR WAFER BY X-RAY DIFFRACTION

[76] Inventors: James C. Fletcher, Administrator of the National Aeronautics and Space Administration, with respect to an invention of Donald L. Parker; Wilbur A. Porter, both of College Station, Tex.

[21] Appl. No.: 724,874

[22] Filed: Sep. 20, 1976

[51] Int. Cl.² .............................................. G01N 23/20
[52] U.S. Cl. ............................... 250/277 CH; 250/280
[58] Field of Search .................. 250/492 A, 280, 275, 250/272, 273, 274

[56] References Cited

U.S. PATENT DOCUMENTS

| | | | |
|---|---|---|---|
| 2,559,972 | 7/1951 | Kerkpatrick | 250/280 |
| 2,585,740 | 2/1952 | Claassen | 250/280 |
| 2,853,617 | 9/1958 | Berreman | 250/280 |

*Primary Examiner*—Craig E. Church
*Attorney, Agent, or Firm*—J. H. Beumer; John R. Manning; L. D. Wofford, Jr.

[57] ABSTRACT

An improved apparatus for examining the crystal lattice of a semiconductor wafer utilizing x-ray diffraction techniques. The apparatus is employed in a method which includes the step of recording the image of a wafer supported in a bent configuration conforming to a compound curve, produced through the use of a vaccum chuck provided for an x-ray camera while the entire surface thereof is illuminated simultaneously by a beam of incident x-rays which are projected from a distant point-source and satisfy conditions of the Bragg Law for all points on the surface of the wafer.

1 Claim, 4 Drawing Figures

U.S. Patent March 7, 1978 4,078,175
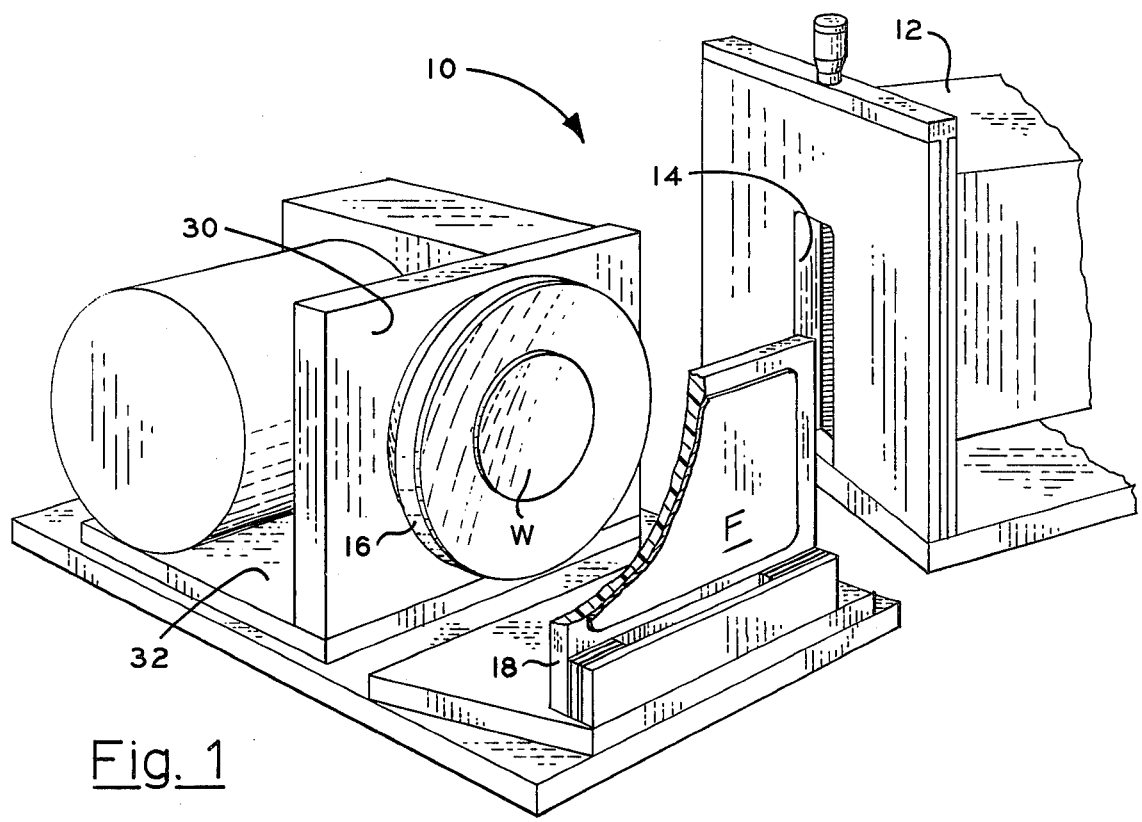
Fig. 1
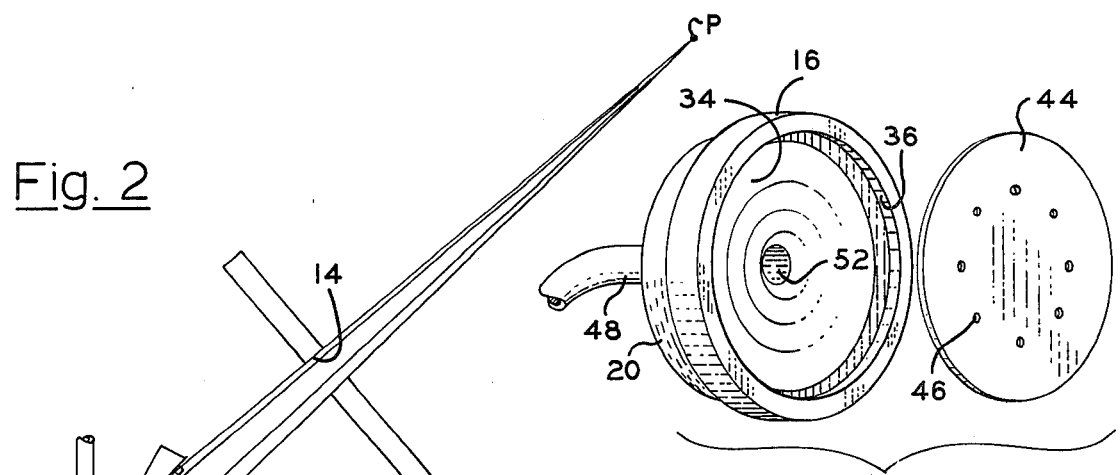
Fig. 2
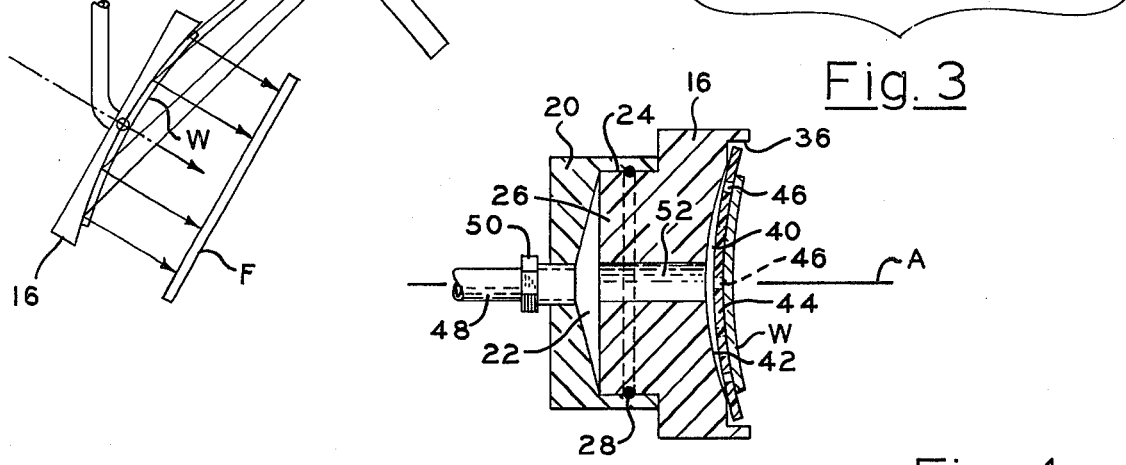
Fig. 3
Fig. 4

APPARATUS FOR USE IN EXAMINING THE LATTICE OF A SEMICONDUCTOR WAFER BY X-RAY DIFFRACTION

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

BACKGROUND OF THE INVENTION

1. Field of the Invention

This invention relates to an apparatus for evaluating semiconductor devices and more particularly to an apparatus which facilitates rapid, nondestructive identification of lattice defects, including strains generated in crystalline semiconductor wafers during the fabrication of semiconductor devices.

As can readily be understood by those familiar with the fabrication of semiconductor devices, each semiconductor wafer is subjected to numerous processing steps during fabrication which tend to introduce defects in the crystalline lattice thereof. These steps include subjecting the wafers to relatively high temperatures in the presence of controlled environments for purposes of enhancing oxide growth, impurity deposition, impurity diffusion, and/or annealing. Lattice defects thus introduced have a predictable effect, to a greater or lesser degree, on the probability that a properly functioning device will be produced, as well as on the overall reliability of that device.

It is therefore advantageous for a manufacturer of semiconductor devices to know which of the processing steps tend to produce lattice defects, and to what degree such defects influence performance so that each processing step which produces lattice defects can be modified to correct improper procedures.

2. Description of the Prior Art

Most presently known techniques employed in determining the degree, distribution, and type of lattice defects present in a given semiconductor wafer are destructive. Consequently, any study relying upon such techniques to determine the effects of lattice defects on the performance of semiconductor devices is necessarily highly statistical. Thus, in order to obtain useful data when employing destructive evaluation techniques, large numbers of wafers must be sacrificed for analysis purposes and considerable effort must be devoted to correlating the resulting data. Hence, it can be appreciated that nondestructive techniques are preferred over those techniques in which a destruction of specimens is required.

One technique heretofore employed in examining semiconductor wafers is a technique referred to as x-ray topography. When employing such a technique it is possible to determine the degree, distribution, and type of existing lattice defect, while no permanent change in the physical, chemical or electrical properties of the semiconductor wafer is introduced.

Studies using this technique, unfortunately, also are statistical in nature. However, the number of specimen samples required for a given confidence level is considerably reduced, since knowledge relating to lattice defects in a given semiconductor wafer may be obtained before and after each processing step.

Although numerous attempts have been made to identify lattice defects using x-ray diffraction, no totally satisfactory solution has resulted from these efforts. For example, the Berg-Barrett technique was first introduced about 1945 in which diffracted rays are caused to leave specimens on the same side as the incoming rays enter. In most current applications of this technique, the specimen and the film are supported in a stationary relationship during exposure. Another technique is the so-called Lang method which was first introduced in 1959 in which the diffracted rays travel through the specimen in reaching a photographic plate. This technique normally requires the specimen and photographic plate be translated to and fro during exposure in order to form an image of a relatively large portion of the specimen. In each of the aforementioned techniques, only an extremely small portion of the total radiation from a small x-ray source is used in the production of an x-ray topograph, thus the costs per x-ray topograph are undesirably high.

Of course, one of the major reasons that x-ray topography is not more widely used as an analytical tool for detection of lattice defects in semiconductor wafers is the high cost per x-ray topograph. In addition to the foregoing reasons for high costs per topograph, high cost of production of a useful x-ray topograph also is due to factors such as the relatively expensive equipment and materials required, as well as in the production thereof, and the necessity that highly trained personnel be employed over relatively long periods.

It is therefore the general purpose of the instant invention to provide an apparatus through a use of which reductions in costs per x-ray topograph of semiconductor wafers is realized.

OBJECTS AND SUMMARY OF THE INVENTION

An object of the invention is to provide an economic apparatus for use in examining the crystal lattice of semiconductor wafers.

It is another object to provide a simple, economic device particularly suited for use in topographically examining the crystal lattice of semiconductor wafers for defects introduced during the production thereof.

It is another object to provide in an apparatus for use in producing an x-ray topograph of a semiconductor wafer a step through which a Rowland focusing condition is achieved by bending the wafer to a compound curved configuration.

It is another object to provide a chuck for use with a topographic camera in which a semiconductor wafer is bent to a compound curved configuration and supported in its bent configuration as x-ray diffraction is employed in examining the lattice defects thereof.

It is another object to provide an improved chuck for bending a semiconductor wafer and supporting the bent wafer in a beam of incident x-rays.

These and other objects and advantages are achieved through a use of a chuck having a vacuum chamber for deforming a semiconductor wafer and supporting the deformed wafer in a beam of incident x-rays, whereby a Rowland focusing condition for x-ray topography is achieved by bending the wafer itself, as will hereinafter become more readily apparent by reference to the following description and claims and in light of the accompanying drawings.

BRIEF DESCRIPTION OF THE DRAWINGS

FIG. 1 is a fragmented, perspective view of a topographic camera having a wafer-supporting chuck which embodies the principles of the instant invention.

FIG. 2 is a schematic view depicting a topographic technique which embodies the principles of the instant invention.

FIG. 3 is a perspective, fragmented view further illustrating the chuck of the instant invention.

FIG. 4 is a cross-sectional view depicting the chuck in a wafer-supporting configuration.

DESCRIPTION OF THE PREFERRED EMBODIMENT

Referring now to the drawings, with more particularity, wherein like reference characters designate like or corresponding parts throughout the several views there is shown in FIG. 1 a fragmented perspective view of a high-speed, x-ray topographic camera, generally designated 10.

The camera 10 is of a type commonly referred to as a Berg-Barrett camera and includes an x-ray scatter tube 12 having a slot through which x-rays propagated from a point-source are projected to strike a wafer W supported by a chuck 16. As shown, the wafer W and slot 14 are so oriented as to cause incident x-rays to strike the wafer at a Bragg angle. The wafer W also is supported by the chuck 16 in a position such that coherently scattered incident x-rays strike a film F supported in close proximity thereto by a suitable film holder 18.

While not shown, it is to be understood that where desired an x-ray detector is employed for purposes of assisting in aligning the camera components preparatory to an operation thereof. Moreover the specific components of the camera 10 are varied as desired. The camera illustrated in the drawings includes an x-ray source known as a G.E. fine focus copper target diffraction tube having a spot projection window with a take-off angle variable from 2° to 6°. The distance of the x-ray source to the center of the wafer W is adjustable from 27 to 30 inches. This requires that the radius of curvature for the wafer be about 97 inches for CuK alpha radiation with a (440) reflection. The Bragg angle for such reflection is 53.35°. The film F currently used is 2½ by 3 inch Kodak Occlusal Ultra-Speed Dental film DF-46, and is placed parallel to and one inch from the wafer W. This distance is chosen so as to position the film as close as possible to the wafer without interfering with the incoming rays, for a two inch diameter wafer. This geometry makes the image size and shape about the same as that of the wafer. The geometric resolution limit is about 15 microns for this camera with the G.E. fine focus tube. The scatter tube is used to limit the direct x-ray beam to an illumination of just the wafer W. No other slits are required. With the aforementioned diffraction tube operating at 40kv and 10ma typical exposure times are one-and-one-half minutes. This, of course, compares very favorably with the several hours of exposure time required for comparable topographs produced employing conventional techniques.

The film holder 18 is supported to be re-positioned as desired for purposes of positioning the film F at required angular relationships with the chuck 16 for accommodating a Bragg condition.

The chuck 16 is, in turn, supported for rotation by a receiver 20 having defined therein a cylindrical chamber 22 having cylindrical internal wall 24. For purposes of achieving a coupling of the chuck 16 to the receiver 20, the chuck is provided with a cylindrical base 26 having an outside diameter substantially equal to the inside diameter of the chamber 22, whereby a friction fit coupling therebetween is achievable. An O-ring 28 is interposed between the contiguous surfaces of the chuck and receiver in a suitably formed groove, not designated. Thus the chuck 16 is supported by the receiver for rotation about an axis, designated A, FIG. 4, passing axially through the wafer W. It is to be understood that the receiver 20 is suitably mounted on a plate 30 affixed to a base 32, by means not shown, so that the chuck 16 is supported to be rotated about an axis, not designated, passing through the wafer's center, perpendicular to the plane of the drawing. Thus the chuck is supported for rotation about a pair of perpendicularly related axes passing through the wafer's center for accommodating Brag scattering.

The chuck 16 includes a retainer 34 defined by an annular lip 36. Symmetrically related with the axis A is a dish-shaped relief 40, defined by a curved surface 42. The surface 42 is of a compound curved configuration having a singular radius of curvature. Where desired, the surface is of a spiral cross section configuration conforming to a specific curvature for purposes of satisfying Bragg conditions at all points on the surface thereof for rays diverging from a distant point-source.

Adapted to be seated in the retainer 34, spanning the relief 40, is a flexible mount 44 which cooperates with the relief 40 to define a vacuum chamber, not designated. The mount 44, preferably, comprises a disc of 150 inch plexiglass, sufficiently flexible to permit it to attain a compound curved configuration having a continuously variable radius of curvature decreasing from infinity to substantially that of the relief 40, in response to a vacuum introduced into the vacuum chamber. This accommodates custom bending of wafers of a variety of crystallographic orientations for satisfying the Rowland focusing condition for some set of diffracting planes. Disposed in an annular array in concentric relation with the center postion of the mount 44 there is a plurality of apertures 46 through which atmosphere is drawn as a vacuum is introduced into the chamber 40. It is important here to understand that the diameter of the array of apertures is slightly less than the diameter of a wafer W to be supported by the mount 44. Thus the apertures 46 are arranged to be positioned near the periphery of the wafer W as the wafer is mounted in the chuck 16.

It should be apparent that as a vacuum is introduced into the chamber 40 a wafer positioned in contiguous relation with the face of the mount 44, in coaxial alignment with the array of apertures 46, will be caused to adhere to the surface of the mount in response to the vacuum introduced between the juxtaposed surfaces of the wafer and the mount.

In order to introduce a vacuum into the chamber 40, the chamber 22 of the receiver 20 is slightly recessed, whereby a plenum chamber, not designated, is caused to be defined in the bottom of the chamber, as best shown in FIG. 4. The chamber 22 is connected in communication with a suitable source of vacuum, not designated, by a tubular conduit 48. The conduit 48 is connected to the receiver 20, by a suitable fitting 50, so that the chamber 22 may be readily vacuumized as a vacuum is introduced therein via the conduit 48.

Similarly, the chuck 16 includes a bore 52 forming a conduit extending between the recess of chamber 22 and the relief 40. Consequently, as a vacuum is drawndown in the chamber 22, the resulting vacuum is introduced into the relief 40, via the conduit 52. It will be appreciated that the vacuum is responsively applied through the array of apertures 46 to the face of the wafer W for holding the wafer in a face-to-face relationship with the mount 44. Thus the wafer continuously is caused to assume substantially any configuration assumed by the mount. It will, therefore, be apparent that the wafer W is deformed to a configuration corresponding to the configuration of the mount as the mount is caused to assume a configuration corresponding to the shape of the curved surface 42, as a vacuum is introduced into the relief 40.

In view of the foregoing, it should readily be apparent that the chuck 16 comprises a novel chuck particularly adapted to bend and then support a semiconductor wafer within the path of a beam of x-rays exiting a scatter tube and striking the wafer at the Bragg angle.

OPERATION

With the chuck 16 connected within the camera 10, in the manner herein before described, a vacuum is introduced into the chamber 22 via the conduit 48. This vacuum is introduced into the relief 40, via the conduit 52. The mount 44, positioned in the retainer 34, is retained in place in response to the pressure differentials existing at its opposite faces as the vacuum is introduced into the chamber 40. The apertures 46, of course, are occluded by a wafer W disposed in contiguous face-to-face engagement with the mount, in coaxial alignment with the array of apertures. Hence, the vacuum is applied to the face of the wafer W for purposes of affixing the wafer W to the mount.

The chuck 16 now is rotated for rotating the wafer, as required, about the two perpendicularly related axes, aforementioned, passing through the wafer's center until Bragg scattering occurs. The vacuum of the vacuum chamber now is increased until Rowland focusing is achieved.

With the chuck 16 so positioned that a Bragg condition is established between the point source P and the curved surface of the wafer, the film F is positioned to intercept coherently scattered x-rays and the image of the wafer W is recorded to provide an economic topograph for use in examining the lattice defects of the wafer.

In view of the foregoing, it should be apparent that the method and apparatus embodying the instant invention provides a practical solution to the perplexing problem of obtaining an economic and practical x-ray examination of lattice defects introduced in semiconductor wafers during fabrication.

We claim:

1. In combination with an x-ray camera, an improved chuck for supporting a semiconductor for illumination by a beam of x-rays, including:
   A. a chuck having
      a concave vacuum chamber characterized by a compound curve configuration having a singular radius of curvature, and
      an annular support surface circumscribing the periphery of the vacuum chamber and circumscribed by an annular lip;
   B. a flexible support plate of a compound curve configuration seated on said annular surface having one face disposed in communicating relation with said vacuum chamber;
   C. means adapted to support a flexible wafer in contiguous relation with the opposite face of the support plate including an annular array of uniformly spaced apertures concentrically related to the center of the support plate establishing communication between said wafer and said vacuum chamber; and
   D. means for maintaining a vacuum within said vacuum chamber.

* * * * *